US00PP36652P2

(12) United States Plant Patent
Tomomatsu et al.

(10) Patent No.: US PP36,652 P2
(45) Date of Patent: May 6, 2025

(54) ***CATHARANTHUS* PLANT NAMED 'CaTU 1915'**

(50) Latin Name: *Catharanthus roseus*
Varietal Denomination: CaTU 1915

(71) Applicants: Koichi Tomomatsu, Shiga (JP); Thunya Taychasinpitak, Nonthaburii (TH); Kenichi Suzuki, Shiga (JP)

(72) Inventors: Koichi Tomomatsu, Shiga (JP); Thunya Taychasinpitak, Nonthaburii (TH); Kenichi Suzuki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/930,850

(22) Filed: Oct. 29, 2024

(51) Int. Cl.
*A01H 5/02* (2018.01)
*A01H 6/08* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Catharanthus* plant named 'CaTU 1915', characterized by its compact, upright and uniformly mounding plant habit; vigorous growth habit; freely basal branching habit; freely flowering habit; long flowering period; relatively small star-shaped purplish red-colored flowers with darker purplish red-colored centers; and good garden performance.

2 Drawing Sheets

Figure 1:
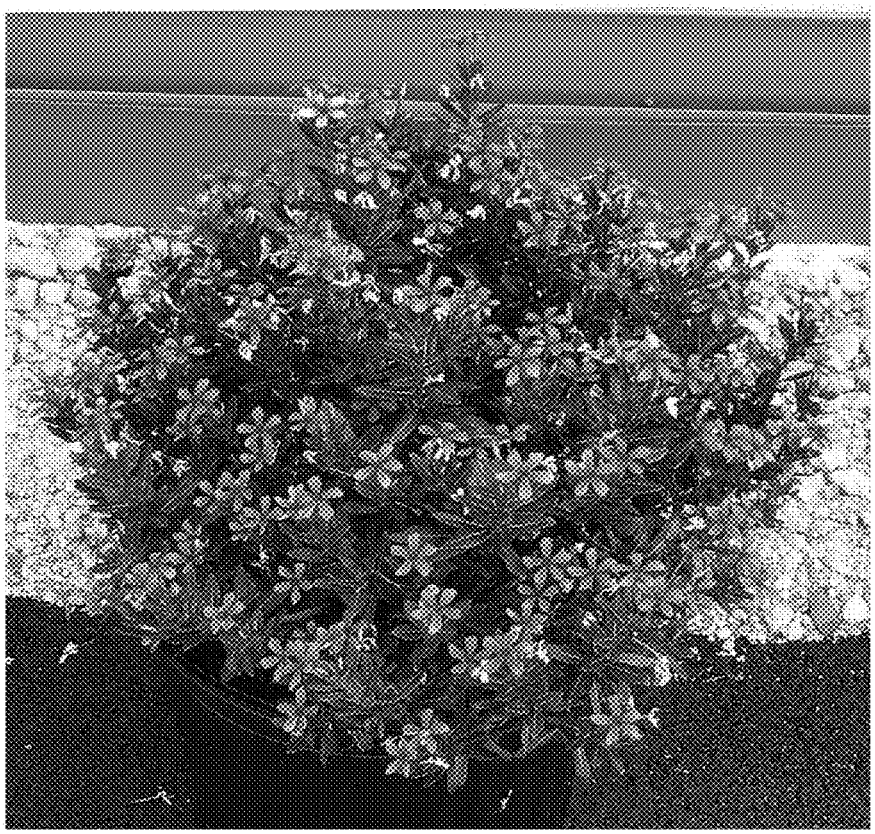

Botanical designation: *Catharanthus roseus.*
Cultivar senomination: 'CaTU 1915'.

BACKGROUND OF THE INVENTION

The present invention relates to a new and distinct *Catharanthus* plant, botanically known as *Catharanthus roseus* and hereinafter referred to by the cultivar name 'CaTU 1915'.

The new *Catharanthus* plant is a product of a planned breeding program conducted by the Inventors in Higashiomi, Shiga, Japan. The objective of the breeding program is to develop new compact and freely branching *Catharanthus* plants with numerous small attractive flowers.

The new *Catharanthus* plant originated from an open-pollination in Higashiomi, Shiga, Japan in June 2018 of a proprietary selection of *Catharanthus roseus* identified as code designation Tu19, not patented, as the female, or seed, parent with an unknown proprietary selection of *Catharanthus roseus* as the male, or pollen, parent. The new *Catharanthus* plant was discovered and selected by the Inventors as a single flowering plant from within the progeny of the stated open-pollination in a controlled greenhouse environment in Higashiomi, Shiga, Japan in February 2019.

Asexual reproduction of the new *Catharanthus* plant by vegetative tip cuttings in a controlled greenhouse environment in Higashiomi, Shiga, Japan since December 2019, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'CaTU 1915'. These characteristics in combination distinguish 'CaTU 1915' as a new and distinct *Catharanthus* plant:

1. Compact, upright and uniformly mounding plant habit.
2. Vigorous growth habit.
3. Freely basal branching habit.
4. Freely flowering habit.
5. Long flowering period.
6. Relatively small star-shaped purplish red-colored flowers with darker purplish red-colored centers.
7. Good garden performance.

Plants of the new *Catharanthus* can be compared to plants of the female parent selection. Plants of the new *Catharanthus* differ primarily from plants of the female parent selection in flower size as plants of the new *Catharanthus* have smaller flowers than plants of the female parent selection. In addition, flower petals of plants of the new *Catharanthus* are narrowly elliptic to oblanceolate in shape whereas flower petals of plants of the female parent selection are broadly obovate to transversely elliptic in shape.

Plants of the new *Catharanthus* can be compared to plants of the *Catharanthus roseus* 'Suncatha 2439', disclosed in U.S. Plant Pat. No. 27,477. In side-by-side comparisons, plants of the new *Catharanthus* differ from plants of 'Suncatha 2439' in the following characteristics:

1. Plants of the new *Catharanthus* are more compact than plants of 'Suncatha 2439'.
2. Plants of the new *Catharanthus* are more upright than plants of 'Suncatha 2439'.
3. Plants of the new *Catharanthus* are more freely branching than plants of 'Suncatha 2439'.

4. Flower petals of plants of the new *Catharanthus* have cuspidate apices whereas flower petals of plants of 'Suncatha 2439' have acute apices.
5. Plants of the new *Catharanthus* have longer peduncles than plants of 'Suncatha 2439'.0

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph on the first sheet (FIG. 1) is a side perspective view of a typical flowering plant of 'CaTU 1915' grown in a container.

Figure 2:
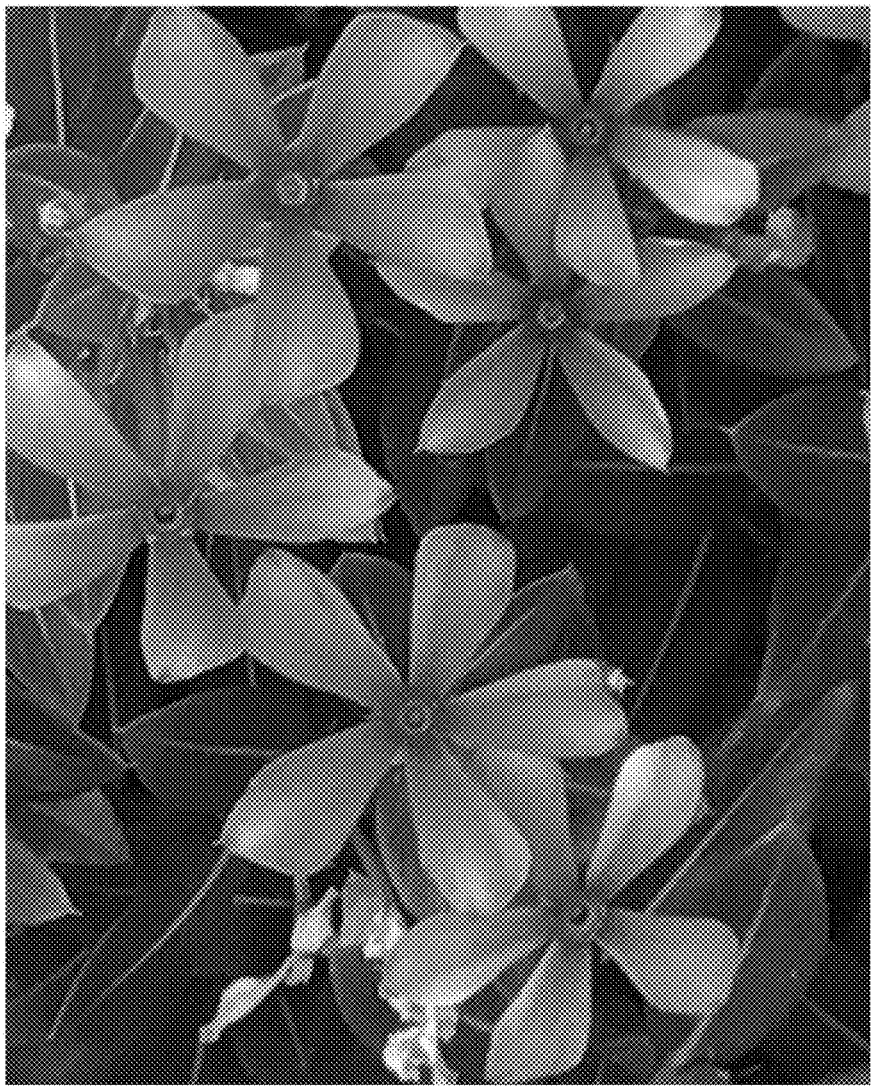

The photograph on the second sheet (FIG. 2) is a close-up view of a typical flowering plant of 'CaTU1915'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs and the description were taken. In the following description, color references are made to The Royal Horticultural Society Colour Chart, 2015 Edition, except where general terms of ordinary dictionary significance are used.

Botanical classification: *Catharanthus roseus* 'CaTU 1915'.

Parentage:

*Female, or seed, parent*.—Proprietary selection of *Catharanthus roseus* identified as code designation Tu19, not patented.

*Male, or pollen, parent*.—Unknown proprietary selection of *Catharanthus roseus*, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright and uniformly mounding plant habit; freely basal branching habit, about seven basal branches each with about twelve secondary branches developing per plant; vigorous growth habit.

*Plant height*.—About 31 cm.

*Plant diameter*.—About 45 cm.

Lateral branch description:

*Length*.—About 23.6 cm.

*Diameter*.—About 2.1 mm.

*Internode length*.—About 1.2 cm.

*Strength*.—Strong.

*Aspect*.—Upright to outwardly.

*Texture*.—Smooth, glabrous.

*Color*.—Close to 144C.

Leaf description:

*Arrangement*.—Opposite, simple.

*Length*.—About 2.8 cm.

*Width*.—About 1 cm.

*Shape*.—Elliptic.

*Apex*.—Acute.

*Base*.—Attenuate.

*Margin*.—Entire.

*Texture, upper and lower surfaces*.—Smooth, glabrous.

*Venation pattern*.—Pinnate; reticulate.

*Color*.—Developing leaves, upper surface: Close to 137A. Developing leaves, lower surface: Close to 137C. Fully expanded leaves, upper surface: Close to 137B; venation, close to 144C. Fully expanded leaves, lower surface: Close to 138B; venation, close to 144D.

*Petioles*.—Length: About 2.5 mm. Diameter: About 1.2 mm. Texture, upper and lower surfaces: Smooth, glabrous. Color, upper and lower surfaces: Close to 144D.

Flower description:

*Flower arrangement and habit*.—Single star-shaped salverform flowers arising from upper leaf axils; freely flowering habit with about four flowers per lateral branch and about 224 flowers developing during the flowering season; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Depending on temperature, individual flowers last about two to three days on the plant; flowers not persistent.

*Flower buds*.—Length: About 2.7 cm. Diameter: About 3 mm. Shape: Ovoid to cylindrical. Color: Distally, close to 64B, and towards the base, close to 138D.

*Flower diameter*.—About 2.3 cm.

*Flower length (depth)*.—About 2 cm.

*Tube length*.—About 1.8 cm.

*Tube diameter, proximally*.—About 1.2 mm.

*Tube diameter, distally*.—About 1.8 mm.

*Corolla*.—Arrangement: Five petals in a single whorl fused at the base into a tube. Petal length from throat: About 1.2 cm. Petal width: About 5.5 mm. Petal eye zone diameter: About 3.2 mm. Petal shape: Narrowly elliptic to oblanceolate. Petal apex: Cuspidate. Petal base: Fused to corolla tube. Petal margin: Entire; not undulate to slightly undulate. Petal texture, upper and lower surfaces: Smooth, glabrous. Throat texture: Smooth, glabrous. Tube texture: Smooth, glabrous. Color: Petal, when opening, upper surface: Close to 71B. Petal, when opening, lower surface: Close to 69D and 70B. Petal, fully opened, upper surface: Close to 71A to 71B; venation, close to 71A to 71B; eye zone, close to 71A. Petal, fully opened, lower surface: Close to 69D and 70B. Throat: Close to 144A and 144B. Tube: Close to 144B and 144C.

*Calyx*.—Arrangement: Star-shaped tubular calyx with five sepals fused towards the base. Sepal length: About 2.3 mm. Sepal width: About 1 mm. Sepal shape: Lanceolate. Sepal apex: Acute. Sepal margin: Entire. Sepal texture, upper and lower surfaces: Smooth, glabrous. Color, upper and lower surfaces: Close to 138A.

*Peduncles*.—Length: About 2.2 mm. Diameter: About 1.2 mm. Angle: Upright to outwardly. Strength: Strong. Texture: Smooth, glabrous. Color: Close to 144B.

*Reproductive organs*.—Stamens: Quantity per flower: Five; filaments fused to the corolla tube. Anther size: About 0.8 mm by 1.4 mm. Anther shape: Narrowly elliptic. Anther color: Close to 8D. Pollen amount: Scarce. Pollen color: Close to 8D. Pistils: Quantity per flower: One. Pistil length: About 1.8 cm. Style color: Close to 145C. Stigma shape: Globose. Stigma color: Close to 145B. Ovary color: Close to 144B. Seeds and fruits: To date, seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: To date, plants of the new *Catharanthus* have not been observed to be resistant to pathogens and pests common to *Catharanthus* plants.

It is claimed:

1. A new and distinct *Catharanthus* plant named 'CaTU 1915' as herein illustrated and described.

* * * * *